(12) United States Patent
Turin

(10) Patent No.: US 7,323,606 B2
(45) Date of Patent: Jan. 29, 2008

(54) AROMACHEMICALS

(75) Inventor: Luca Turin, London (GB)

(73) Assignee: Flexitral, Inc., Chantilly, VA (US)

( * ) Notice: Subject to any disclaimer, the term of this patent is extended or adjusted under 35 U.S.C. 154(b) by 0 days.

(21) Appl. No.: 11/356,300

(22) Filed: Feb. 17, 2006

(65) Prior Publication Data
US 2006/0210503 A1 Sep. 21, 2006

(51) Int. Cl.
C07C 27/10 (2006.01)
(52) U.S. Cl. .............................. 568/700; 512/8; 424/65
(58) Field of Classification Search ................ 568/700; 512/89; 424/65
See application file for complete search history.

(56) References Cited

U.S. PATENT DOCUMENTS 4,587,129 A  5/1986 Kliment

FOREIGN PATENT DOCUMENTS

| WO | WO 01/06853 A3 | 1/2001 |
| WO | WO 01/06853 A2 | 2/2001 |
| WO | WO 03/053902 A | 7/2003 |

OTHER PUBLICATIONS

Skattebol, Lars et al.: Insect Juvenile Hormone Analogues and Their Biological Activity on Sea Lice (Lepeophtheirus salmonis); Journal of Agricultural and Food Chemistry, vol. 52, 2004, pp. 6944-6949, XP002390740; p. 6945, "Materials and Methods"; p. 6946, Scheme 2; p. 6947, compound 23.
http://europa.eu.int/comm/enterprise/chemicals/legislation/detergents/legislation/allergenic_subst.pdf or http://www.leco.org/customersupport/apps/separationscience/-236.pdf].
Vogel's textbook of Practical Organic Chemistry 5th Edition (1989) pp. 1106-1108.
Solomon's Organic Chemistry 4th Edition pp. 342 and 343, published by John Wiley and Sons.
Solomon's Organic Chemistry 4th Edition pp. 837 and 843, published by John Wiley and Sons.
S. Arctander, Perfume and Flavor Chemicals, 1969, Montclair, N.J., USA.
J. Agric. Food Chem., 2004, vol. 52, Skattebol et al., pp. 6944-6949. See Scheme 2.

Primary Examiner—Yvonne Eyler
Assistant Examiner—Sudhakar Katakam
(74) Attorney, Agent, or Firm—Womble Carlyle Sandridge & Rice

(57) ABSTRACT

The present invention provides a compound having one of the following formulae:

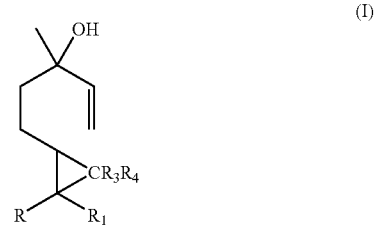

(I)

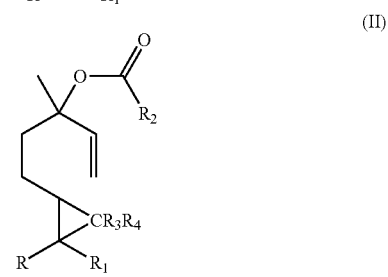

(II)

R and $R_1$ are each independently H or $C_{1-5}$ alkyl provided that in formula (I) when R is methyl, $R_1$ is H or $C_{2-5}$ alkyl. $R_2$ has from 1 to about 12 carbon atoms and is a straight or branched aliphatic group, or a cyclic, heterocyclic or aromatic group. $R_3$ and $R_4$ are each independently H or $CH_3$. Mixtures of these compounds, methods for their preparation, their use as perfume materials for application to a variety of substrates and their use in flavoring and in articles of manufacture is also provided.

24 Claims, No Drawings

AROMACHEMICALS

The present invention relates generally to the field of flavors and fragrances. More particularly, the present invention relates to improved derivatives of conventional compounds that provide perfumes and other articles with properties and advantages not shared by the conventional compounds from which they are derived. These derivatives find utility in any and all applications requiring the flavors and fragrances supplied by the conventional compounds from which they are derived. The invention also provides mixtures of these derivatives, methods for their preparation and their use as perfume materials for application to a variety of substrates and their use in flavoring and articles of manufacture including the derivatives.

There are a large number and variety of known flavors and fragrances used as ingredients in perfumes and in a varied range of other products. For example, perfumes for application in laundry detergents, fabric softeners, rinse conditioners and other products intended for use on textile fibers primarily contain fragrances. However, many aromachemicals include double bonds and/or other reactive groups which are potentially susceptible to reaction and may result in a limited useful lifetime. Further, many essential oil fragrances have recently been determined to cause allergic reactions, and it is becoming increasingly difficult to bring products containing such fragrances to market.

Linalool is a widely used fragrance/flavorant due to its highly prized odor profile: natural floral character [floral-woody with faint citrus note]. Ethyl Linalool is also highly popular, having a lavender, bergamot, coriander character. It is more floral, sweeter and less agrestic than Linalool. As with Linalool, it is used in a wide variety of notes for floral bouquets.

Linalool acetate has a sweet green citrus, bergamot, lavender, woody character and is also a very popular fragrance/flavorant.

The use of these compounds has recently been undercut, however, by the discovery that the molecules have a relatively high allergenic quotient. [See for example http://europa.eu.int/comm/enterprise/chemicals/legislation/detergents/legislation/allergeric_subst.pdf or http://www.leco.org/customersupport/apps/separationscience/-236.pdf].

The listing or discussion of a prior-published document in this specification should not necessarily be taken as an acknowledgement that the document is part of the state of the art or common general knowledge.

It is an object of the invention to provide novel derivatives of the conventional aromachemical compounds mentioned above and related compounds. The derivatives typically possess similar odor profiles to the conventional compounds but are not as highly allergenic and/or have improved useful lifetimes. In some instances, the derivatives may also have improved odor intensity and/or stability.

The present invention provides compounds of formula (I) and formula (II):

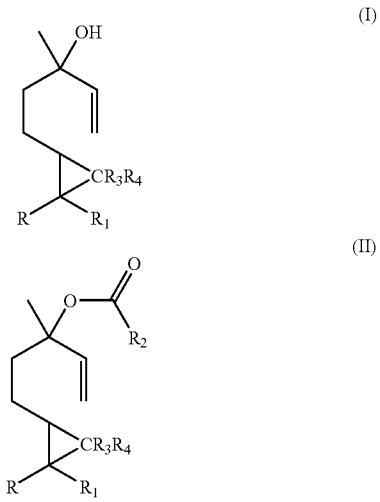

wherein R and $R_1$ are each independently H or $C_{1-5}$ alkyl provided that in formula (I) when R is methyl, $R_1$ is H or $C_{2-5}$ alkyl; $R_2$ has from 1 to about 12 carbon atoms and is a straight or branched aliphatic group, or a cyclic, heterocyclic or aromatic group; and $R_3$ and $R_4$ are each independently H or $CH_3$.

Preferably $R_2$ is, alkyl, alkenyl, alkoxy, aryl or arlyloxy having up to 12 carbon atoms. If $R_2$ is a heterocyclic group, suitable heteroatoms include oxygen, nitrogen and sulphur. In other words, $R_2$ is the residue of an esterifying aliphatic, heterocyclic or aromatic carboxylic acid having from 1 to about 12 carbon atoms. For example, the ester may be an acetate, acetoacetate, anthranilate, benzoate, butyrate, iso-butyrate, caproate, caprylate, cinnamate, citronellate, crotonate, ethoxyacetate, formate, furoate, heptoate, N-methylanthranilate, methyltiglate, methoxyacetate, nonanoate, pelargonate, pentanoate, phenylacetate, propionate, pyruvate, salicylate, tiglate, valerate or iso-valerate.

The groups R and $R_1$ may be the same or different. If R and/or $R_1$ is a $C_{1-5}$ alkyl group they may each independently contain 1, 2, 3, 4 or 5 carbon atoms and may be straight or branched or cyclic.

Compounds of formula (I) in which one of R or $R_1$ is methyl and the other one of R and $R_1$ is alkyl having 2, 3, 4 or 5 carbon atoms are preferred. For example, R may be methyl and $R_1$ may be ethyl (a cyclopropanated derivative of ethyl linalool).

In the compounds of formula (II), it is preferable that at least one of R and $R_1$ is methyl. For example both R and $R_1$ may be methyl. Preferred compounds of Formula II are those in which $R_2$ is a straight or branched $C_{1-12}$ alkyl group, more preferably a $C_{1-6}$ alkyl group, for example an alkyl group having 1, 2, 3, 4, 5 or 6 carbon atoms.

Particularly preferred compounds of formula (II) are those in which R and $R_1$ are both methyl and $R_2$ is methyl (i.e. the compound of formula (II) may be a cyclopropanated derivative of linalool acetate). Examples of other compounds of formula (II) in which R or $R_1$ is methyl include compounds in which the other one of R and $R_1$ is hydrogen or $C_{3-5}$ alkyl. Other preferred compounds of formula (II) include cyclopropanated derivatives of linalyl anthranilate, linalyl benzoate, linalyl cinnamate, linalyl formate, linalyl isobutyrate, linalyl phenyl acetate, and linalyl propionate.

In the compounds of formulae (I) and (II), $R_3$ and $R_4$ may be the same or different. In other words, both $R_3$ and $R_4$ may be H or one of $R_3$ and $R_4$ may be H and the other one may be methyl or $R_3$ and $R_4$ may both be methyl.

Specific examples of compounds of formulae (I) include:

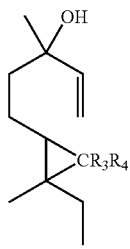

wherein $R_3$ and $R_4$ are both H or are both methyl or one of $R_3$ and $R_4$ is H and the other one is methyl, i.e. cyclopropanated derivatives of ethyl linalool.

Specific examples of compounds of formulae (II) include:

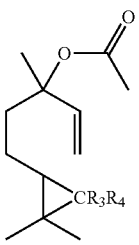

wherein $R_3$ and $R_4$ are both H or are both methyl or one of $R_3$ and $R_4$ is H and the other one is methyl, i.e. cyclopropanated derivatives of linalool acetate.

As used herein, the term "cyclopropanated derivative" or "cyclopropane derivative" includes any and all of methyl, dimethyl and unsubstituted cyclopropane derivatives, i.e. any possible combination of $R_3$ and $R_4$.

The present invention also provides a method for synthesizing the compounds of formula (I) and formula (II).

The compounds of the invention can be prepared from the "parent" aromachemicals or in the case of the esters of formula (II) from the corresponding alcohol but do not need to proceed in this manner. That is, the compounds can be derived from synthetic strategies that do not involve the "parent" aromachemicals.

The compounds of formula (1) may be prepared by the cyclopropanation of a parent compound of formula:

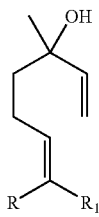

wherein R and $R_1$ are as defined above for the compounds of formula (I).

Any suitable method of cyclopropanation known in the art may be used. The 6,7-double bond in the parent compounds that are typically used to produce the compounds of the invention is relatively electron-rich. Thus any cyclopropanation reaction that proceeds readily at an electron-rich double bond may be used. Suitable methods include carbonoid reactions such the Simmon-Smith (Zn—Cu couple) cyclopropane synthesis (see for example Vogel's textbook of Practical Organic Chemistry $5^{th}$ Edition (1989) pp 1106-1108 or Solomon's Organic Chemistry $4^{th}$ Edition pp 342 and 343, published by John Wiley and Sons). The Friedricks reaction, which uses diethylzinc and an acyl chloride as a catalyst or halocarbene reactions also may be used. Alternatively, compounds of formula (I) can be synthesized by subjecting the parent compound to the haloform reaction to produce the dichloro or dibromo cyclopropyl derivative followed by dehalogenation with, e.g., lithium to the desired product.

This method of producing the compounds of formula (I) is summarised in the following reaction scheme:

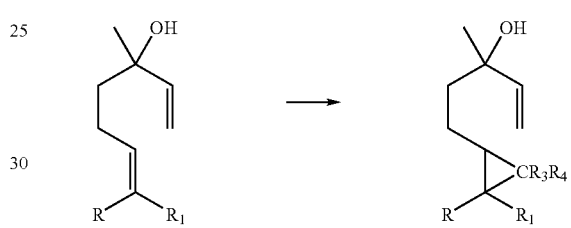

wherein R and $R_1$ are as defined above for the compounds of formula (I).

More specifically, the cyclopropanation of ethyl linalool can be illustrated as follows:

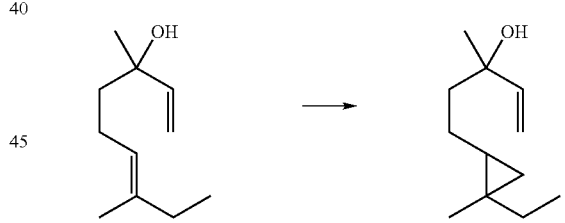

The compounds of formula (II) may be prepared by the cyclopropanation of the corresponding alcohol of formula:

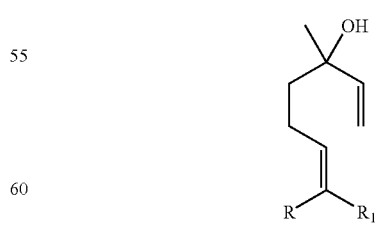

wherein R and $R_1$ are as defined above for the compounds of formula (II) followed by esterification of the hydroxyl group. Any suitable method of cyclopropanation such as one of the methods described above may be used. Any suitable esterification method known in the art may be used. For example, the esters can be obtained by the reaction of the alcohol with an appropriate acyl chloride. Other methods of esterification are described in for example Solomon's Organic Chemistry 4$^{th}$ Edition pp 837 and 843, published by John Wiley and Sons.

This method for producing a compound of formula (II) can be summarised as follows:

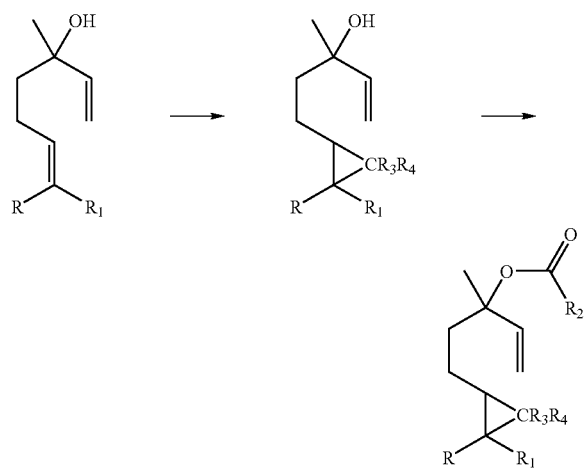

wherein R and $R_1$ are as defined above for formula (II).

More specifically, the preparation of a cyclopropanated derivative of linalool acetate can be illustrated as follows:

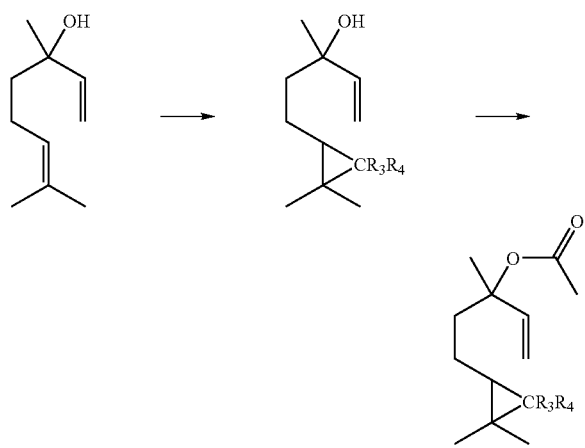

The compounds of the invention have at least two chiral centres. The carbon atom bearing the OH or ester group and the carbon at the 6-position are both chiral. If R and $R_1$ are different, the carbon at the 7-position will also be chiral. If $R_3$ and $R_4$ are different, the carbon atom bearing these groups will also be chiral. Any reference herein to the compounds of the invention is intended to refer to mixtures such as racemic mixtures of the stereoisomers and to the individual stereoisomers. If necessary, the individual stereoisomers can be separated using techniques well known in the art.

The present invention is predicated on the realisation that the compounds of the invention possess substantially the same flavorant/odor profiles as the parent aromachemicals but substantially less of the allergenic characteristics of the parent aromachemicals. Hydroperoxides formed by autooxidation of linalool or related compounds at the 6,7-double bond have been implicated as powerful sensitizers, and have resulted in restrictions on the use of these compounds and their esters. That electron-rich, readily oxidisable double bond is absent in the compounds of the invention, and its potential for sensitizer formation is therefore reduced or even eliminated.

The compounds of the invention can be considered to be "isodonic" to the compounds from which they are derived. By this we mean that they have essentially the same odor profile. However, they typically have improved stability, odor intensity and/or other improved physical and/or chemical properties.

The present invention provides for the use of the compounds of the invention and mixtures thereof as a flavor and/or fragrance.

The present invention also provides compositions, products, preparations or articles having improved aroma, fragrance or odor characteristics containing a compound or mixture of compounds of the invention as described above.

The present invention also provides methods to confer, improve, enhance or modify the taste or flavor property of a composition, product, preparation or article which comprises adding thereto a flavor effective amount of a composition or mixture of compounds of the invention as described above.

A method to confer, improve, enhance or modify the aroma, fragrance or odor characteristics of compositions, products, preparations or articles which comprises adding thereto an aroma, fragrance or odor effective amount of a composition or mixture of compounds of the invention as described above is also provided.

The compounds of the invention can be included in virtually any article of manufacture that can include the non-derivatized fragrance or flavorant compound, or for that matter, other fragrances, whether natural or artificial. Examples include bleach, detergents, flavorings and fragrances, beverages, including alcoholic beverages, and the like. The compounds of the invention can be used in applications like soaps, shampoos, body deodorants and antiperspirants, solid or liquid detergents for treating textiles, fabric softeners, detergent compositions and/or all-purpose cleaners for cleaning dishes or various surfaces, for both household and industrial use. Of course, the use of the compounds is not limited to the above-mentioned products, as they be used in other current uses in perfumery, namely the perfuming of soaps and shower gels, hygiene or hair-care products, as well as of body deodorants, air fresheners and cosmetic preparations, and even in fine perfumery, namely in perfumes and colognes.

The compounds of the invention also find utility in foods, flavorings, beverages such as beer and soda, denture cleansers (tablets), flavored orally-delivered products such as lozenges, candies, chewing gums, matrices, pharmaceuticals and the like. These uses are described in more detail below.

The compounds of the invention can be used as perfuming ingredients, as single compounds or as mixtures thereof, preferably in an amount of at least about 30% by weight of the perfume composition, more preferably in an amount of at least about 60% by weight of the composition. The compounds can be used in their pure state or as mixtures, without added components. The olfactive characteristics of the individual compounds are also present in mixtures thereof, and mixtures of these compounds can be used as perfuming ingredients. This may be particularly advantageous where separation and/or purification steps can be avoided by using compound mixtures.

In all of the above applications, the compounds of the invention can be used alone, in admixture with each other, or in admixture with other perfuming ingredients, solvents or adjuvants of current use in the art. The nature and the variety of these co-ingredients do not require a more detailed description here, which, moreover, would not be exhaustive, and the person skilled in the art will be able to choose the latter through their general knowledge and as a function of the nature of the product to be perfumed and of the desired olfactive effect.

These perfuming ingredients typically belong to chemical classes as varied as alcohols, aldehydes, ketones, esters, ethers, acetates, nitriles, terpene hydrocarbons, sulfur- and nitrogen containing heterocyclic compounds, as well as essential oils of natural or synthetic origin. A large number of these ingredients described in reference textbooks such as the book of S. Arctander, Perfume and Flavor Chemicals, 1969, Montclair, N.J., USA, the contents of which are hereby incorporated by reference in its entirety, or its more recent versions, or in other works of similar nature.

The proportions in which the compounds of the invention can be incorporated in the various products vary within a large range of values. These values depend on the nature of the article or product that one desires to perfume and the odor effect searched for, as well as on the nature of the co-ingredients in a given composition when the compounds are used in admixture with perfuming co-ingredients, solvents or adjuvants of current use in the art.

As an example, the compounds of the invention are typically present at concentrations between about 0.1 and about 10%, or even more, by weight of these compounds relative to the weight of the perfuming composition in which they are incorporated. Far lower concentrations than those mentioned above can be used when the compounds are directly applied for perfuming the various consumer products mentioned above.

The compounds may be used in detergents containing bleaching agents and activators such as, for example, tetraacetylethylenediamine (TAED), hypohalites, in particular hypochlorite, peroxygenated bleaching agents such as, for example, perborates, etc. The compounds can also be used in body deodorants and antiperspirants, for example, those containing aluminum salts. These aspects are described in more detail below.

In addition to the compounds of the invention, the compositions herein may include a detersive surfactant and optionally, one or more additional detergent ingredients, including materials for assisting or enhancing cleaning performance, treatment of the substrate to be cleaned, or to modify the aesthetics of the detergent composition (e.g. perfumes, colorants, dyes, etc.). Non-limiting examples of synthetic detersive surfactants useful herein typically at levels from about 0.5% to about 90%, by weight, include the conventional $C_{1-18}$ alkyl benzene sulfonates ("LAS") and primary, branch-chain and random $C_{10-20}$ alkyl sulfates ("AS"), and the like. Preferred compositions incorporating only synthetic detergents have a detergent level of from about 0.5% to 50%. Compositions containing soap preferably comprise from about 10% to about 90% soap.

The compositions described herein can contain other ingredients such as enzymes, bleaches, fabric softening agents, dye transfer inhibitors, suds suppressors, and chelating agents, all well known within the art.

The compounds of the invention can be incorporated into beverages and impart various flavorings to the beverages. The beverage composition can be a cola beverage composition, and can also be coffee, tea, dairy beverage, fruit juice drink, orange drink, lemon-lime drink, beer, malt beverages, or other flavored beverage. The beverages can be in liquid or powdered form. The beverage compositions can also include one or more flavoring agents; artificial colorants; vitamin additives; preservatives; caffeine additives; water; acidulants; thickeners; buffering agents; emulsifiers; and/or fruit juice concentrates.

Artificial colorants that may be used include caramel color, yellow 6 and yellow 5. Useful vitamin additives include vitamin B2, vitamin B6, vitamin B12, vitamin C (ascorbic acid), niacin, pantothenic acid, biotin and folic acid. Suitable preservatives include sodium or potassium benzoate. Salts that may be used include sodium, potassium and magnesium chloride. Exemplary emulsifiers are gum arabic and purity gum, and a useful thickener is pectin. Suitable acidulants include citric, phosphoric and malic acid, and potential buffering agents include sodium and potassium citrate.

The beverage may, for example, be a carbonated cola beverage. The pH is generally about 2.8 and the following ingredients can be used to make the syrup for these compositions: Flavor Concentrate, including one or more of the compounds of the invention herein (22.22 ml), 80% Phosphoric Acid (5.55 g), Citric Acid (0.267 g), Caffeine (1.24 g), artificial sweetener, sugar or corn syrup (to taste, depending on the actual sweetener) and Potassium Citrate (4.07 g). The beverage composition can be prepared, for example, by mixing the foregoing syrup with carbonated water in a proportion of 50 ml syrup to 250 ml of carbonated water.

Flavored food and pharmaceutical compositions including one or more of the compounds of the invention can also be prepared. The compounds of the invention can be incorporated into conventional foodstuffs using techniques well known to those of skill in the art. Alternatively, the compounds can be incorporated within polymeric particles, which can, in turn, be dispersed within and/or over a surface of an orally-deliverable matrix material, which is usually a solid or semi-solid substrate. When used in chewable compositions, the compounds of the invention can be released into the orally-deliverable polymeric matrix material as the composition is chewed and held in the mouth, thus prolonging the flavor of the composition. In the case of dried powders and mixes, the flavor can be made available as the product is consumed or be released into the matrix material as the composition is further processed. When two flavors are combined with the polymeric particles, the relative amounts of the additives can be selected to provide simultaneous release and exhaustion of the compounds.

Flavored compositions of the invention may include an orally-deliverable matrix material; a plurality of water insoluble polymeric particles dispersed in the orally-deliverable matrix material, where the polymeric particles individually define networks of internal pores and are non-degradable in the digestive tract;

and one or more compounds of the invention entrapped within the internal pore networks. The compounds of the invention are released as the matrix is chewed, dissolved in the mouth, or undergoes further processing selected from the group consisting of liquid addition, dry blending, stirring, mixing, heating, baking, and cooking. The orally-deliverable matrix material can be selected from the group consisting of gums, latex materials, crystallized sugars, amorphous sugars, fondants, nougats, jams, jellies, pastes, powders, dry blends, dehydrated food mixes, baked goods, batters, doughs, tablets, and lozenges.

A flavorless gum base can be combined with a compound or a mixture of compounds of the invention to a desired flavor concentration. In one method for producing such gum based products a blade mixer is heated to about 110° F., the gum base is preheated so that it is softened, and the gum base is then added to the mixer and allowed to mix for approximately 30 seconds. The compound or compounds of the invention are then added to the mixer and mixed for a suitable amount of time. The gum can be then removed from the mixer and rolled to stick thickness on waxed paper while warm.

The compounds of the invention may be incorporated into a system that can release a fragrance in a controlled manner. These include substrates such as air fresheners, laundry detergents, fabric softeners, deodorants, lotions, and other household items. The fragrances are generally one or more derivatives of essential oils as described herein, each present in different quantities. U.S. Pat. No. 4,587,129, the contents of which are hereby incorporated by reference in their entirety, describes a method for preparing gel articles that contain up to 90% by weight of fragrance or perfume oils. The gels are prepared from a polymer having a hydroxy (lower alkoxy) 2-alkeneoate, a hydroxy (lower alkoxy) lower alkyl 2-alkeneoate, or a hydroxy poly (lower alkoxy) lower alkyl 2-alkeneoate and a polyethylenically unsaturated crosslinking agent. These materials have continuous slow release properties, i.e. they release the fragrance component continuously over a long period of time. Advantageously, all or a portion of those derivatives that include an aldehyde group can be modified to include an acetal group, which can cause the formulations to release fragrance over a period of time as the acetal hydrolyzes to form the aldehyde compound.

The present invention is illustrated by the following non-limiting example.

EXAMPLE 1

To a mixture of Linalool in anhydrous N-hexane and potassium tert-butoxide (3.0 eq) was added CHBr$_3$ (2.0 eq), dropwise under a nitrogen atmosphere at −20° C., over two hours. The temperature of the mixture then was raised to room temperature and stirred overnight.

Brine was added and the solution extracted with petroleum ether. The combined organic extracts were dried over Na$_2$SO$_4$, filtered, evaporated to yield the dibromocyclopropane derivative of linalool.

To a solution of the above dibromocyclopropane derivative in anhydrous THF and anhydrous tert-butanol (4.4 eq) was added lithium granules (11 eq), portion-wise, at 40° C. The mixture was stirred 30 minutes at that temperature then warmed to 75° C. for an appropriate time period. The mixture was added to brine slowly, extracted with petroleum ether, dried over Na$_2$SO$_4$ and evaporated to yield the cyclopropane derivative of linalool.

The cyclopropane derivative of linalool was then reacted with acetyl chloride to produce the cyclopropanated derivative of linalool acetate.

Having hereby disclosed the subject matter of the present invention, it should be apparent that many modifications, substitutions, and variations of the present invention are possible in light thereof. It is to be understood that the present invention can be practiced other than as specifically described. Such modifications, substitutions and variations are intended to be within the scope of the present application.

The invention claimed is:

1. A compound having one of the following formulae:

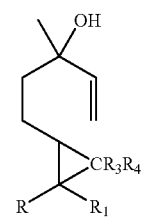

(I)

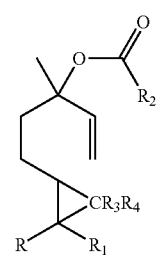

(II)

wherein R and R$_1$ are each independently H or C$_{1-5}$ alkyl provided that in formula (I) when R is methyl, R$_1$ is H or C$_{2-5}$ alkyl; R$_2$ has from 1 to 12 carbon atoms and is a straight or branched chain aliphatic group, or a cyclic; heterocyclic or aromatic group; and R$_3$ and R$_4$ are each independently H or CH$_3$.

2. A compound according to claim 1 of formula (I), wherein R is methyl and R$_1$ is ethyl.

3. A compound according to claim 1 of formula (II), wherein R, R$_1$ and R$_2$ are each methyl.

4. A method of producing a compound of formula (I) as defined in claim 1, which comprises cyclopropanating a parent compound of formula:

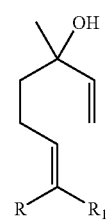

wherein R and R$_1$ are as defined for formula (I).

5. A method of producing a compound of formula (II) as defined in claim 1, which comprises cyclopropanating a parent compound of formula:

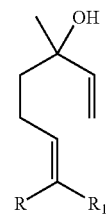

wherein R and R$_1$ are as defined for formula (II) to produce a product of formula:

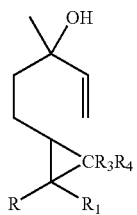

and esterifying that product to produce a compound of formula (II).

6. A method for treating a substrate to impart flavorant/fragrance releasing characteristics thereto comprising treating the substrate with a compound as defined in claim 1.

7. A composition having aroma, fragrance or odor releasing characteristics containing a compound or mixture of compounds as defined in claim 1.

8. A composition according to claim 7, wherein the compound or mixture of compounds is present in an amount of at least 30 percent by weight.

9. A composition according to claim 8, wherein the compound or mixture of compounds is present in an amount of at least 60 percent by weight.

10. A composition according to claim 7 in the form of a perfume, fragrance or cologne, a soap, a bath or shower gel, a shampoo or other hair care product, a cosmetic preparation, a body odorant, deodorant or antiperspirant, an air freshener, a liquid or solid fabric detergent or softener, bleach product, disinfectant or an all-purpose household or industrial cleaner.

11. A composition according to claim 10, in the form of a liquid or solid fabric detergent.

12. A composition according to claim 10, in the form of a bleach product.

13. A composition according to claim 10, in the form of a disinfectant product.

14. A composition according to claim 10, in the form of a body odorant, deodorant or antiperspirant product.

15. A composition according to claim 7, in the form of a beverage.

16. A composition according to claim 7, in the form of a flavoring product.

17. A composition according to claim 7, in the form of a food.

18. A composition according to claim 7, in the form of a chewing gum.

19. A composition according to claim 7, in the form of a pharmaceutical product.

20. A composition according to claim 7, in the form of an orally-deliverable matrix material.

21. A method to modify a taste or flavor property of a composition, which comprises adding thereto a flavor effective amount of a compound or mixture of compounds as defined in claim 1.

22. A method according to claim 21, wherein said composition, is in the form of a beverage, a flavoring, a food, a chewing gum, a pharmaceutical or an orally deliverable matrix.

23. A method to modify an aroma, fragrance or odor characteristics of a composition, which comprises adding thereto an aroma, fragrance or odor effective amount of a compound or mixture of compounds as defined in claim 1.

24. A method according to claim 23 wherein said composition, is in the form of a perfume, a body odorant, deodorant or antiperspirant, a detergent, a bleach product or a disinfectant.

* * * * *